United States Patent
Sakano et al.

(10) Patent No.: US 8,283,480 B2
(45) Date of Patent: Oct. 9, 2012

(54) PERFLUOROPOLYETHER GROUP-CONTAINING ACRYLATE COMPOUND

(75) Inventors: Yasunori Sakano, Annaka (JP); Yuji Yamane, Annaka (JP); Noriyuki Koike, Takasaki (JP); Hirofumi Kishita, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 316 days.

(21) Appl. No.: 12/797,103

(22) Filed: Jun. 9, 2010

(65) Prior Publication Data
US 2010/0317875 A1 Dec. 16, 2010

(30) Foreign Application Priority Data
Jun. 10, 2009 (JP) ................. 2009-139158

(51) Int. Cl.
C07F 7/21 (2006.01)
C07F 7/08 (2006.01)
C07F 7/10 (2006.01)

(52) U.S. Cl. ........................ 549/214; 556/419

(58) Field of Classification Search .......... None
See application file for complete search history.

(56) References Cited

U.S. PATENT DOCUMENTS
2007/0116971 A1  5/2007  Yoshikawa et al.

FOREIGN PATENT DOCUMENTS
| JP | 5-194322 A | 8/1993 |
| JP | 7-118279 A | 5/1995 |
| JP | 11-349651 A | 12/1999 |

OTHER PUBLICATIONS

European Search Report dated Sep. 30, 2010 for Application No. 10165314.5.
Honda et al., "Surface Molecular Aggregation Structure and Surface Properties of Poly(fluoroalkyl acrylate) Thin Films," Kobunshi Ronbunshu, vol. 64, No. 4, Apr. 2007, pp. 181-190 (English Abstract on p. 190).

*Primary Examiner* — Yevegeny Valenrod
(74) *Attorney, Agent, or Firm* — Birch, Stewart, Kolasch & Birch, LLP

(57) ABSTRACT

The present invention relates to a photo-curable perfluoropolyether group-containing acrylate compound represented by the following formula (1):

$$X^1-[Z-Rf-Z-X^2]_y-Z-Rf-Z-X^1 \quad (1)$$

wherein Rf is a divalent perfluoropolyether group;
$X^1$ is a group represented by the following formula (2):

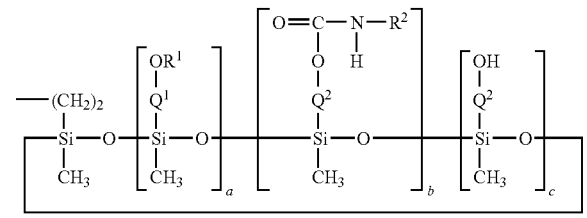

(2)

$R^2$ is a group represented by the following formula (4):

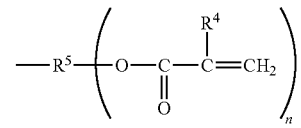

(4)

$X^2$ is a group represented by the following formula (5):

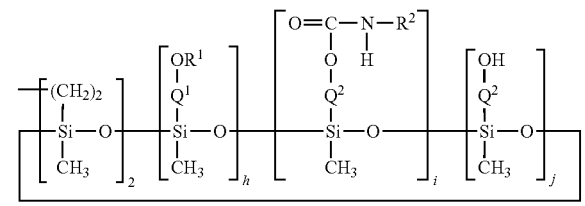

(5)

and Z is a divalent organic group.

20 Claims, No Drawings

PERFLUOROPOLYETHER GROUP-CONTAINING ACRYLATE COMPOUND

CROSS REFERENCE

This application claims the benefits of Japanese Patent Application No. 2009-139158 filed on Jun. 10, 2009, the contents of which are incorporated herein by reference.

FIELD OF THE INVENTION

The present invention relates to an acrylate compound which has a photo-curable perfluoropolyether group, specifically an acrylate compound which has cyclic siloxane structure and good compatibility with non-fluorine solvents, hereinafter referred to as "a fluorine-containing acrylate".

BACKGROUND OF THE INVENTION

Polymers composed of polymerizable monomer which has a perfluoroalkyl group in a side chain, such as a fluorine-containing alkyl ester of acrylic acid and a fluorine-containing alkyl ester of methacrylic acid, are widely known as a fluorine compound which can be cured by radiation of light, such as ultraviolet rays. As a typical example, an acrylate which has the following structure has widely been used in order to provide a substrate surface with water- and oil-repellency, stain resistance, abrasion resistance and scratch resistance.

$$C_8F_{17}-CH_2-CH_2-O-\underset{\underset{O}{\|}}{C}-\underset{\underset{CH_3}{|}}{C}=CH_2$$

However, recently, there is an increasing tendency with environmental concerns to regulate use of compounds which have a long-chain perfluoroalkyl group containing eight or more carbon atoms. Meanwhile, it is known that acrylic compounds having a perfluoroalkyl group with less than eight carbon atoms give a worse surface property than ones having a perfluoroalkyl group with eight or more carbon atoms do (the following Non-Patent Literature 1).

Meanwhile, photo-curable fluorine compounds are known which have a perfluoropolyether group composed of an oxygen atom which forms an ether bond and a perfluoroalkyl group containing three or less carbon atoms in series. For instance, Patent Literature 1 discloses the following acrylic compound which is derived from a hexafluoropropylene oxide oligomer.

$$CF_3CF_2CF_2-O-\underset{\underset{CF_3}{|}}{C}FCF_2-O-CF_2CF_2CH_2CH_2O\underset{\underset{O}{\|}}{C}-CH=CH_2$$

Patent Literature 2 discloses a urethane acrylate which is a reaction product of a fluorine-containing polyether diol with 2-isocyanatoethyl methacrylate. However, the urethane acrylate has bad compatibility with photo polymerization initiators, non-fluorinated acrylates and non-fluorinated organic solvents due to the water- and oil-repellency of the fluorine-containing compounds and, therefore, can be blended with a restricted number of components and has restricted usage.

[Patent Literature 1]: Japanese Patent Application Laid-Open No. Hei-5-194322

[Patent Literature 2]: Japanese Patent Application Laid-Open No. Hei-11-349651

[Non-Patent Literature 1]: Koubunshi Ronbun-Shu Vol. 64, No. 4, pp 181-190 (April, 2007).

SUMMARY OF THE INVENTION

Problems to be Solved by the Invention

The purpose of the present invention is to provide a photo-curable fluorine compound which has good compatibility with non-fluorine organic compounds, maintaining good properties as a fluorine compound.

Means to Solve the Problem

Namely, the present invention is as follows.

The present invention is a perfluoropolyether group-containing acrylate compound represented by the following formula (1), $$X^1-[Z-Rf-Z-X^2]_y-Z-Rf-Z-X^1 \qquad (1)$$

wherein Rf is a divalent perfluoropolyether group with a molecular weight of from 500 to 30000, optionally having branched structure;

$X^1$ is, independently of each other, a group represented by the following formula (2);

$$-(CH_2)_2-\underset{\underset{CH_3}{|}}{\overset{\overset{OR^1}{|}}{Si}}-O-\left[\underset{\underset{CH_3}{|}}{\overset{\overset{OR^1}{|}}{\underset{\underset{}{|}}{Si}}-O}\right]_a\left[\underset{\underset{CH_3}{|}}{\overset{\overset{O=C-N-R^2}{\underset{\underset{O}{|}}{\overset{|}{\underset{H}{}}}}}{\underset{\underset{}{|}}{Si}}-O}\right]_b\left[\underset{\underset{CH_3}{|}}{\overset{\overset{OH}{|}}{\underset{\underset{}{|}}{Si}}-O}\right]_c \qquad (2)$$

wherein a and c are an integer of from 0 to 4;

b is an integer of from 1 to 4, provided that a total of a, b and c is 2, 3 or 4;

$R^1$ is, independently of each other, a group represented by the following formula (3), $$-(C_4H_8O)_d(C_3H_6O)_e(C_2H_4O)_f(CH_2O)_gR^3 \qquad (3)$$

wherein d, e, f and g are, independently of each other, an integer of from 0 to 20, provided that a molecular weight of $R^1$ is in a range of 30 to 600;

the repeating units may be sequenced at random; and $R^3$ is a saturated or unsaturated hydrocarbon residue having 1 to 10 carbon atoms;

$R^2$ is an acryl group- or alpha-substituted acryl group-containing group represented by the following formula (4);

$$-R^5-\left(O-\underset{\underset{O}{\|}}{C}-\underset{\underset{}{|}}{\overset{\overset{R^4}{|}}{C}}=CH_2\right)_n \qquad (4)$$

wherein R⁴ is, independently of each other, a hydrogen atom, a fluorine atom, a methyl group or a trifluoromethyl group;

R⁵ is a divalent or trivalent linking group having 1 to 18 carbon atoms, optionally having an ether bond and/or ester bond; and n is an integer of 1 or 2;

$Q^1$ and $Q^2$ may be same with or different from each other and are a divalent linking group with 3 to 20 carbon atoms, optionally having an ether bond, an ester bond, an amide bond or a urethane bond and optionally having cyclic or branched structure;

$X^2$ is, independently of each other, a group represented by the following formula (5),

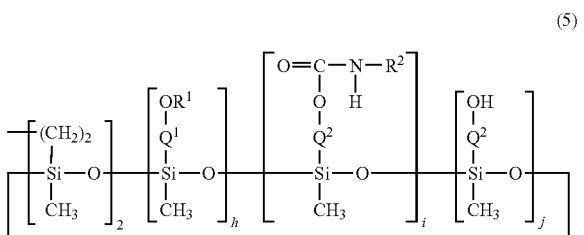

(5)

wherein $R^1$, $R^2$, $Q^1$ and $Q^2$ are as defined above;

h, i and j are an integer of from 0 to 3, provided that a total of h, i and j is an integer of from 1 to 3; and the repeating units may be sequenced at random;

Z is a divalent organic group, optionally containing an oxygen atom, a nitrogen atom or a fluorine atom and an unsaturated bond, and optionally having cyclic structure; and v is an integer of from 0 to 5.

Effects of the Invention

The present fluorine-containing acrylate is good in compatibility with non-fluorinated organic compounds and, further, can be cured by light to form a cured product which is water- and oil-repellent. Accordingly, the present acrylate is useful as an additive for hard coats.

BEST MODES OF THE INVENTION

The present invention will be explained in detail below.

The fluorine-containing acrylate of the present invention is represented by the following formula (1).

$$X^1-[Z-Rf-Z-X^2]_v-Z-Rf-Z-X^1 \quad (1)$$

In formula (1), Rf is a divalent perfluoropolyether residue having a molecular weight of from 500 to 30000, optionally having branched structure. Rf may be a divalent perfluoropolyether group having 1 to 500 repeating units represented by the general formula $-C_iF_{2i}O-$, wherein i is, independently of each other among the units, an integer of from 1 to 6, preferably a perfluoropolyether group represented by the following formulas (6) to (8).

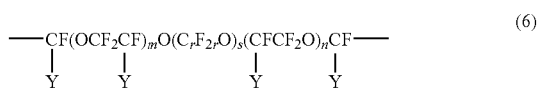

(6)

In formula (6), Y is, independently of each other, a fluorine atom or a $CF_3$ group; r is an integer of from 2 to 6; and m and n are each an integer of from 0 to 200, provided that a total of m and n is 2 to 200. s is an integer of from 0 to 6, wherein the repeating units may be sequenced at random.

(7)

In formula (7), j is an integer of from 1 to 3 and k is an integer of from 1 to 200.

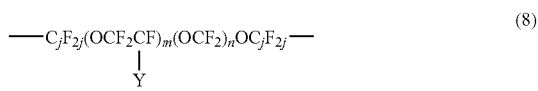

(8)

In formula (8), Y is a fluorine atom or a $CF_3$ group; j is an integer of from 1 to 3; and m and n are each integer of from 0 to 200, provided that a total of m and n is from 2 to 200. The repeating units may be sequenced at random.

In formula (1), $X^1$ is, independently of each other, a group represented by the following formula (2).

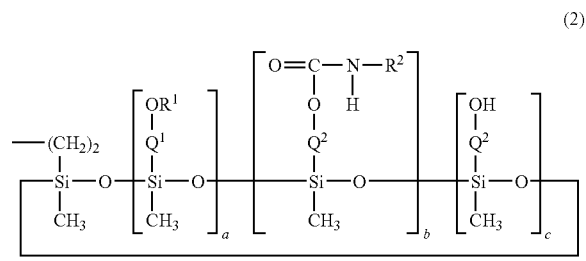

(2)

In formula (2), a and c are an integer of from 0 to 4 and b is an integer of from 1 to 4, provided that a total of a, b and c is an integer of 2, 3 or 4.

In formula (2), $Q^1$ and $Q^2$ may be same with of different from each other and are a divalent linking group with 3 to 20 carbon atoms, optionally having an ether bond, an ester bond, an amide bond or a urethane bond. $Q^1$ and $Q^2$ may optionally have cyclic or branched structure. $Q^1$ and $Q^2$ may preferably be the groups represented by the following formulas.

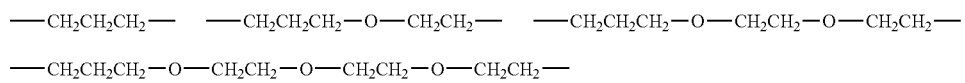

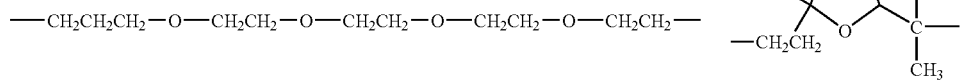

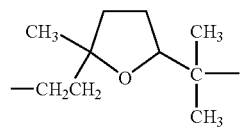

In formula (2), $R^1$ is, independently of each other, represented by the following formula (3):

wherein $R^3$ is a saturated or unsaturated hydrocarbon residue having 1 to 10 carbon atoms and c, d, e and f are, independently of each other, an integer of from 0 to 20, preferably from 1 to 10, provided that a molecular weight of $R^1$ is in a range of from 30 to 600, preferably from 60 to 300. The repeating units may be sequenced at random.

$R^3$ is a saturated or unsaturated hydrocarbon residue having 1 to 10 carbon atoms. Mention may be of a methyl group, an ethyl group, a propyl group, an isopropyl group, a butyl group, a pentyl group, a hexyl group, a 2-ethylhexyl group, a cyclohexyl group, a phenyl group and a benzyl group, particularly preferably a methyl group and an ethyl group.

$R^1$ is preferably a group represented by the following formula:

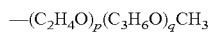

wherein p and q are an integer of from 0 to 20, provided that a total of p and q is from 1 to 40, the propylene group may be branched and the repeating units may be sequenced at random.

$R^2$ is a monovalent organic group with 1 to 20 carbon atoms having at least one acryl group or at least one alpha-substituted acryl group, as represented by the following formula (4).

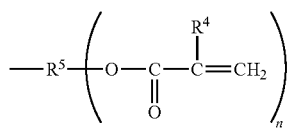

In formula (4), $R^4$ is, independently of each other, a hydrogen atom, a fluorine atom, a methyl group or a trifluoromethyl group, particularly preferably a hydrogen atom or a methyl group. $R^5$ is a divalent or trivalent linking group having 1 to 18 carbon atoms and may optionally contain oxygen atom which forms an ether bond, ester structure, acryl group structure or methacryl group structure. Preferred is a group represented by the following formulas, particularly those comprising an ethylene group. n is an integer of 1 or 2.

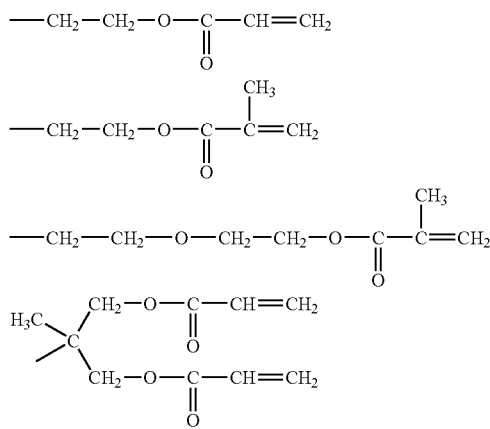

In formula (1), $X^2$ is, independently of each other, represented by the following formula (5):

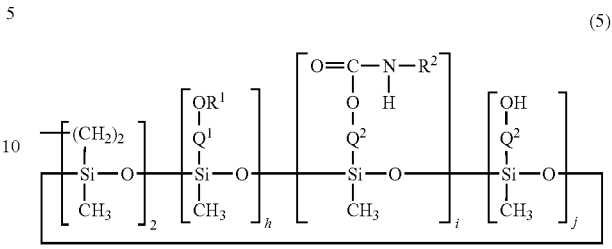

wherein $R^1$, $R^2$, $Q^1$ and $Q^2$ are as defined above;

h, i and j are an integer of from 0 to 3, provided that a total of h, i and j is an integer of from 1 to 3; and the repeating units may be sequenced at random.

In formula (1), Z is a divalent organic group and may optionally contain an oxygen atom, nitrogen atom or fluorine atom and an unsaturated bond. Z may have cyclic structure. v is an integer of from 0 to 5. Z is not particularly limited as far as it does not hinder the polymerization of the acryl group. Examples of Z include the following groups.

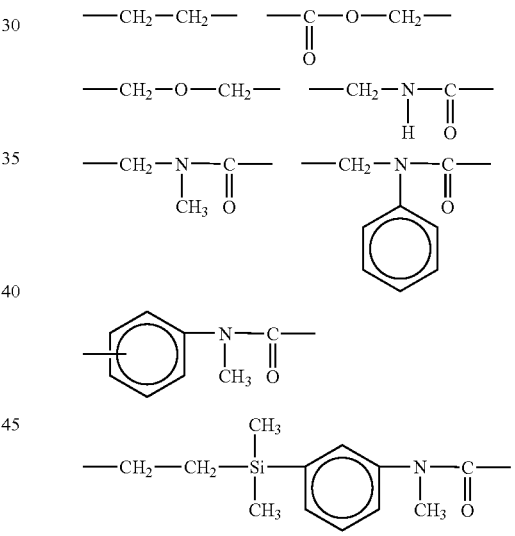

Among these, the following groups are particularly preferred.

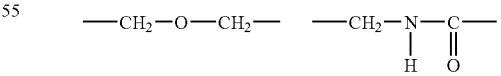

The fluorine-containing acrylate described above can be prepared in the following process.

First, a perfluoropolyether compound olefinated at both ends as represented by the following formula (9):

wherein Rf and Z are as defined above, is subjected to addition reaction with a cyclic hydrogen siloxane represented by the following formula (10):

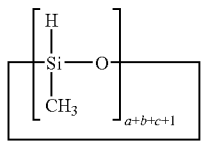

(10)

wherein a, b and c are as defined above,
in the presence of a catalyst at a temperature of from 60 to 150 degrees C., preferably from 70 to 120 degrees C., to obtain a poly-functionalized SiH compound having a perfluoropolyether group, as represented by the following formula (11):

$$W^1[Z-Rf-Z-W^2]_v-Z-Rf-Z-W^1 \quad (11)$$

wherein Rf, Z and v are as defined above.
In formula (11), $W^1$ is represented by the following formula.

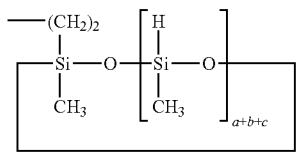

wherein a, b and c are as defined above.
In formula (11), $W^2$ is represented by the following formula.

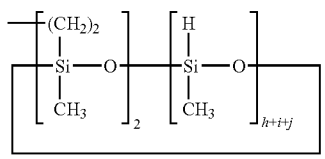

wherein h, i and j are as defined above and the repeating units in $W^2$ may be sequenced at random.

The addition reaction may be carried out without a solvent, but a solvent may be used for dilution, if needed. The solvent for dilution does, preferably, not interfere with hydrosilylation and can dissolve compound (11) resulting from the reaction. Preferred are those which can dissolve both of the compounds (9) and (10) at a desired reaction temperature, such as fluorine-modified solvents, e.g., fluorine-modified aromatic hydrocarbons, such as m-xylenehexafluoride and benzotrifluoride, and fluorine-modified ether solvents such as methyl perfluorobutyl ether and perfluoro(2-butyltetrahydrofurane), inter alia, m-xylenehexafluoride.

As the catalyst, use may be made of compounds which comprise, for instance, platinum, rhodium or palladium, particularly, compounds which comprise platinum, such as hexachloroplatinate (IV) hexahydrate, a platinum carbonyl vinyl methyl complex, a platinum-divinyltetramethyldisiloxane complex, a platinum-cyclovinylmethylsiloxane complex, a platinum-octylaldehyde/octanol complex or platinum supported on activated coal. The catalyst is blended preferably in such an amount that the amount of the metal is from 0.1 to 5000 ppm, more preferably from 1 to 1000 ppm, relative to the amount of compound (9).

In the addition reaction, the components may be fed in any order. For example, a mixture of compounds (9) and (10) with a catalyst is gradually heated from room temperature to a temperature of addition reaction; a mixture of compounds (9) and (10) with a diluting solvent is heated to a desired reaction temperature and, then, a catalyst is added dropwise; a mixture of compounds (10) with a catalyst is heated to a desired reaction temperature and, then, compound (9) is added dropwise; or compound (10) is heated to a desired reaction temperature and, then, a mixture of compound (9) with a catalyst is added dropwise. Among these, preferred are the method where a mixture of compounds (9) and (10) with a diluting solvent is heated to a desired reaction temperature and, then, a catalyst is added dropwise; and the method where compound (10) is heated to a desired reaction temperature and, then, a mixture of compound (9) with a catalyst is added dropwise. In these methods, each component or a mixture may be diluted with a solvent, if needed.

The amount of compound (10) to be added relative to compound (9) may be any amount as far as v in compound (II) is an integer of from 0 to 5. Preferably, compound (9) is reacted with compound (10) of at least two times the amount of compound (9) and, then, unreacted compound (10) is distilled off under a reduced pressure so as to avoid three-dimensional cross linking. The reaction is preferably carried out with 1 to 10 equivalents, particularly 2 to 6 equivalents, of compound (10) per equivalent of an allyl group of compound (9). If needed, an intermediate having a smaller v is prepared and, then, addition reaction may further be carried out in a stepwise manner. For instance, compound (II) with v=0 is first prepared and, then, 2 moles of this compound (II) is reacted with 1 mole of compound (9) to obtain compound (II) with v=3. Alternatively, a component with a desired value of v may be separated from a mixture of components with various values of v by any separation means.

Then, an olefin compound represented by the following formula (12) and optionally an olefin compound represented by the following formula (13) are hydrosilylated with compound (11).

$$V-Q^3-OH \quad (12)$$

$$V-Q^3-OR^1 \quad (13)$$

V is an olefin group which can addition react with an Si—H group. $Q^3$ is, independently of each other, a divalent linking group having 1 to 18 carbon atoms and may have an ether bond, an ester bond, an amide bond or a urethane bond. $Q^3$ may have cyclic or branched structure and may be same with or different from each other. $R^1$ is as defined above.

In the case where compounds (12) and (13) are addition reacted with compound (II), compound (II) is desirably addition reacted first with compound (13), then with an excess amount of compound (12) and, subsequently, unreacted compound (12) is removed for purification. Here, compounds (12) and (13) each may be a mixture of compounds where V, $Q^3$ or $R^1$ is different from each other. A compound represented by the following formula (14) is obtained.

$$U^1-[Z-Rf-Z-U^2]_v-Z-Rf-Z-U^1 \quad (14)$$

$U^1$ in formula (14) is represented by the following group.

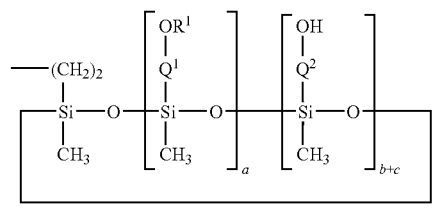

wherein a, b and c are as defined above.

U² in formula (14) is represented by the following group.

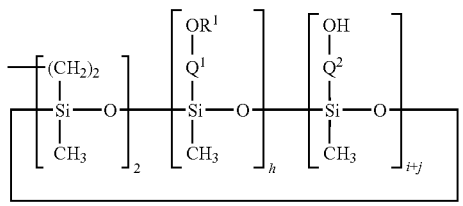

wherein h, i and j are as defined above.

All or some of the hydroxyl groups in the afore-mentioned formula (14) may be reacted with an isocyanate compound represented by the following formula (15):

$$R^2-N=C=O \quad (15)$$

wherein $R^2$ is as defined above,
to form a urethane bond so that a fluorine-containing acrylate compound having the structure of formula (1) is obtained.

The reaction of compound (II) with compound (12) and/or (13) may proceed by mixing them at a temperature of 0 to 120 degrees C. A suitable catalyst may be added to accelerate a reaction rate. Examples of the catalyst include alkyltin ester compounds such as dibutyltin diacetate, dibutyltin dilaurate, dibutyltin dioctanoate, dioctyltin diacetate, dioctyltin dilaurate, dioctyltin dioctanoate and stannous dioctanoate; titanate esters or titanium chelate compounds, such as titanium tetraisopropoxide, titanium tetra-n-butoxide, titanium tetrakis(2-ethylhexoxide), titanium dipropoxybis(acetylacetonato) and titanium isopropoxyoctylene glycol; and zirconium chelate compounds such as zirconium tetraacetylacetonate, zirconium tributoxymonoacetylacetonate, zirconium monobutoxyacetylacetonate bis(ethylacetoaceate), zirconium dibotoxybis(ethylacetoacetate) and zirconium tetraacetylacetonate. One or more of these may be used. The catalyst is used in an amount of 0.01 to 2% by mass, preferably 0.05 to 1% by mass, relative to a total weight of the reactants to accelerate a reaction rate. If desired, reaction may be carried out under dilution with a suitable solvent. Any solvent may be used as long as it does not react with an isocyanato or and hydroxyl group. Specific examples include ethers such as tetrahydrofuran, diisopropyl ether and dibutyl ether.

The present compound is blended in a composition for a hard coat to provide the coating with stain resistance, a fingerprint proof property, water repellency and oil repellency. The amount of compound (1) to be added is 0.01 to 20 parts by mass, preferably 0.05 to 10 parts by mass, relative to 100 parts by mass of effective components in a non-fluorine composition for a hard coat. If the amount exceeds the afore-mentioned upper limit, a layer of a fluorine-containing acrylate component become so thick that performance as a hard coat may be impaired. Below the afore-mentioned lower limit, the surface of a hard coat layer cannot be covered sufficiently.

Any composition for a hard coat of a non-fluorine type may be used as long as it is miscible with the present compound and curable. A major agent is preferably urethane acrylate. As the urethane acrylates, mention may be made of
a reaction product of a polyisocyanate with a (meth)acrylate having a hydroxyl group;
a reaction product of a polyisocyanate, a polyester having terminal diols and a (meth)acrylate having a hydroxyl group; and
a reaction product of a polyol, an excess amount of diisocyanate and a (meth)acrylate having a hydroxyl group. Inter alia, a urethane acrylate is preferred which is a reaction product of a (meth)acrylate having a hydroxyl group selected from 2-hydroxyethyl(meth)acrylate, 2-hydroxy-3-acryloyloxypropylmethacrylate and pentaerythritol triacrylate with a polyisocyanate selected from hexamethylene diisocyanate, isophorone diisocyanate, trilene diisocyanate and diphenylmethane diisocyanate.

Examples of the other compositions for a hard coat include one whose major component comprises di- to hexa-functional (meth)acrylic compounds such as 1,6-hexanediol di(meth)acrylate, neopentyl glycol di(meth)acrylate, ethylene glycol di(meth)acrylate, ethylene oxide isocyanurate-modified di(meth)acrylate, EO-isocyanurate modified tri(meth)acrylate, trimethylolpropane tri(meth)acrylate, pentaerythritol tri(meth)acrylate, glycerol tri(meth)acrylate, tris(meth)acryloyloxyethyl phosphate, (2,2,2-tri-(meth)acryloyloxymethyl)ethyl hydrogen phthalate, glycerol tri(meth) acrylate, pentaerythritol tetra(meth)acrylate, ditrimethylolpropane tetra(meth)acrylate, dipentaerythritol penta(meth)acrylate, dipentaerythritol hexa(meth)acrylate and sorbitol hexa(meth)acrylate; epoxyacrylates obtained by addition reaction of the afore-mentioned (meth)acrylic compounds with ethylene oxide, propylene oxide, epichlorohydrin or an aliphatic acid-, alkyl- or urethane-modified epoxy resin; and acrylate ester copolymers which have a (meth)acryloyl group in their side chain.

Various hard coat materials which can be cured with active energy rays, such as ultraviolet rays or electron beam, are commercially available from various companies. For instance, mention may be made of various trade names, such as "Beam Set" ex Arakawa Chemical Industries Ltd.; "Ubiq" ex Oohashi Chemical Industries Ltd.; "UV coat" ex Origin Electric Co., Ltd.; "Cashew UV" ex Cashew Co., Ltd.; "DeSolite" ex JSR Corporation; "Seika Beam" ex Dainichiseika Chemical Industries Co., Ltd.; "Shikoh" ex The Nippon Synthetic Chemical Industry Co., Ltd.; "Fujihard" ex Fujikura Kasei Co., Ltd.; "Diabeam" ex Mitsubisi Rayon Co., Ltd.; and "Ultra Vin" ex Musashi Paint Co., Ltd. The present compound can also be blended in a fluorinated type of a composition for a hard coat to increase, for instance, water repellency and oil repellency.

The present compound is useful to provide the surface of a hard coat layer with stain resistance, water repellency, oil repellency and a fingerprint proof property by adding the present compound to a composition for a hard coat. The hard coat surface is obtained which is not easily stained with fat of human being such as fingerprint, sebum and sweat, and cosmetics. Even when stain attaches to the coat, the stain is easily wiped off. Accordingly, the present compound can be used as an additive for curable compositions which are to be coated on a surface of articles which surface may be touched by a human body and stained with human fat or cosmetics, to form a coating film or protective film thereon. Examples of the articles include optical recording media such as optical discs and hologram records, for instance, optical magnetic discs, CD's, LD's, DVD's and blue ray discs; optical parts and optical devices such as lenses of glasses, prisms, lens sheet, pellicle films, polarizing plates, optical filters, lenticular lenses, Fresnel lenses, antireflection films, optical fibers and optical couplers; screens or displaying devices such as CRT's, liquid crystal displays, plasma displays, electroluminescence displays, rear projection displays, fluorescent display tubes (VFD's), field emission projection displays and toner displays, particularly, image-displaying devices such as personal computers, mobile phones, personal digital assistants, game machines, digital cameras, digital camcorders, automated teller machines, cash dispensers, automatic vending machines, navigation devices of, for instance, automobiles and security system terminals and devices for displaying and inputting an image of touchpanel type with which the operation thereof is also carried out, such as touch sensors and touchscreens; inputting devices such as mobile phones, personal digital assistants, mobile music players and handheld game machines, remote controllers, controllers, key boards and panel switches for in-car-devices; surfaces of housing of mobile phones, personal digital assistants, cameras, mobile music players and handheld game machines; coatings and surfaces of exteriors of automobiles, pianos, classy furniture and marble stones; parts made of transparent glass or plastic (acryls or polycarbonates) and various mirror members such as protective glass for exhibiting works of art, show windows, show cases, covers for advertisement, covers for photo stands, wrist watches, windshields for automobiles, window glass for trains and air planes, headlights and tail lamps of automobiles.

The acrylate compound of the present invention which has a perfluoropolyether group can be added to a UV-curable liquid resist and exposed to light to cause big difference on liquid repellency between a surface of the resist after cured and a part where the resist was removed. Therefore a developing liquid or a liquid crystal solution does not remain on the surface of the resist resin, so that the surface is prevented from being stained.

EXAMPLES

The present invention will be specifically explained by the following Examples, but shall not be limited thereto.

Example 1

In a 2000 ml three-necked flask equipped with a reflux device and a stirrer were placed 500 g of perfluopolyether having alpha-unsaturated bonds on both ends, represented by the following formula (16), 700 grams of m-xylenehexafluoride and 361 grams of tetramethylcyclotetrasiloxane under a dry nitrogen atmosphere and heated with stirring up to 90 degrees C. Then, 0.442 grams of a solution of a chloroplatinic acid/vinylsilsoxane complex in toluene (platinum content: $1.1 \times 10^{-6}$ mole) was added and the stirring was continued for 4 hours while keeping the inner temperature at 90 degrees C. or higher. Disappearance of the peak of the allyl group of the starting material was confirmed with $^1$H-NMR and, then the solvent and the unreacted tetramethylcyclotetrasiloxane were removed under reduced pressure and treated with active carbon to obtain 498 grams of a colorless and transparent, liquid, perfluoropolyether-containing compound represented by the following formula (17), hereinafter referred to as "compound I".

$$CH_2{=}CH{-}CH_2{-}O{-}CH_2{-}Rf{-}CH_2{-}O{-}CH_2{-}CH{=}CH_2 \quad (16)$$

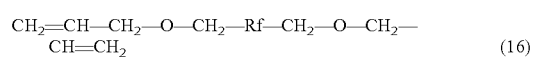

(p/q=0.9 p+q≈45)

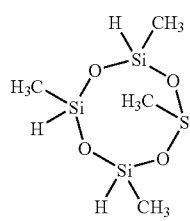―CH₂―CH₂―CH₂―O―CH₂―Rf―CH₂―O―CH₂―CH₂―CH₂―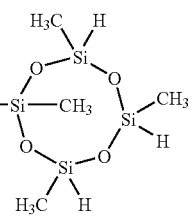

(17)

50.0 Grams of compound (I) were mixed with 7.05 grams of 2-allyloxyethanol, 50.0 grams of m-xylenehexafluoride and 0.0442 gram of a solution of chloroplatinic acid/vinyl siloxane complex in toluene (Pt content: $1.1 \times 10^{-7}$ mole) under a dry air atmosphere and stirred at 100 degrees C. for 4 hours. Disappearance of the Si—H group was confirmed with $^1$H-NMR and IR and, then, the solvent and unreacted 2-allyloxyethanol were distilled off under reduced pressure and treated with active carbon to obtain 55.2 grams of a liquid, pale yellow, perfluoropolyether-containing compound, hereinafter referred to as "compound II".

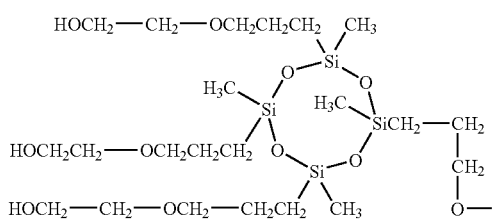―CH₂―Rf―CH₂―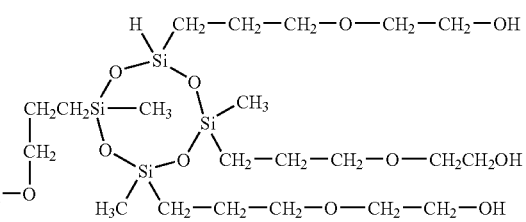

(18)

50.0 Grams of compound (II) were mixed with 50.0 grams of THF and 9.00 grams of 2-acryloyloxyethyl isocyanate under a dry air atmosphere and heated to 50 degrees C. Then, 0.05 gram of dioctyltin laurate was added and stirred at 50 degrees C. for 24 hours. After the completion of the heating, distillation was carried out under reduced pressure of 2 Torr to obtain 58.7 grams of a pasty pale yellow material, hereinafter referred to as "compound III". $^1$H-NMR and IR spectra showed that the material was a compound represented by the following formula (19).

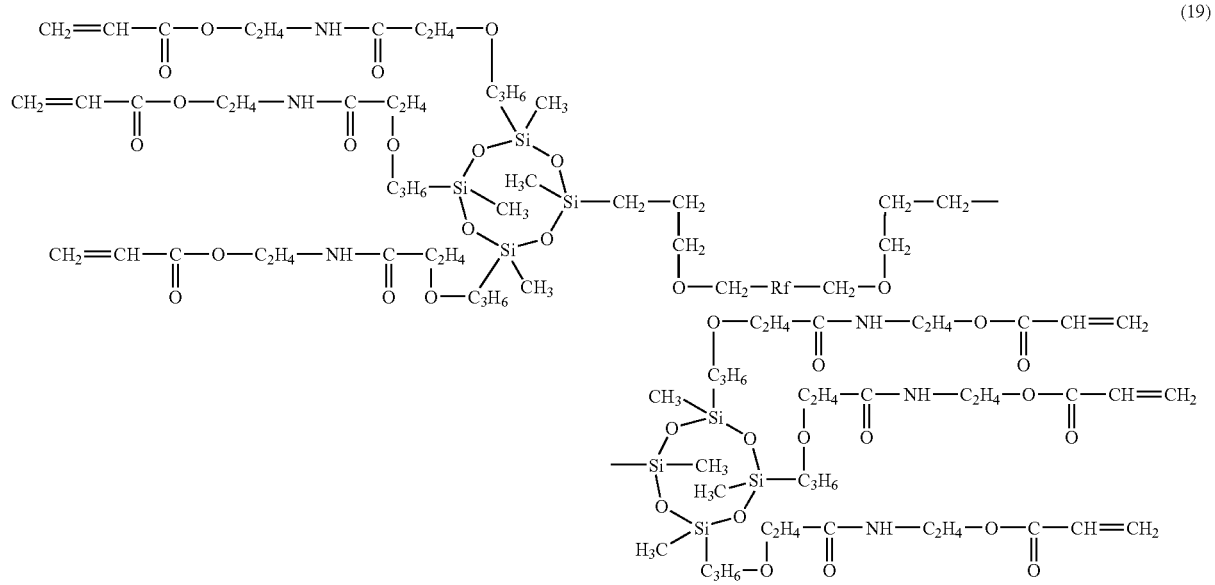

(19)

Chemical shifts in $^1$H-NMR spectrum are shown in Table 1. (Measuring device: JMN-LA300W ex JEOL, solvent: $CDCl_3$)

TABLE 1

| Shift (TMS Reference) | |
|---|---|
| 0~0.2 ppm | —Si—CH$_3$ 24H |
| 0.4~0.7 ppm | —Si—$\overline{CH_2}$—CH$_2$—CH$_2$—O— 16H |
| 1.4~1.7 ppm | —Si—$\overline{CH_2}$—CH$_2$—CH$_2$—O— 16H |
| 3.1~4.0 ppm | —Si—CH$_2$—$\overline{CH_2}$—CH$_2$—O— 16H |
| | —Si—CH$_2$—CH$_2$—$\overline{CH_2}$—O—CH$_2$— 16H |
| | —NH—CH$_2$—CH$_2$—O— 12H |
| 4.0~4.3 ppm | —Si—$\overline{CH_2}$—CH$_2$—CH$_2$—O—CH$_2$—CH$_2$—O—CONH—CH$_2$—CH$_2$—O—CO— 24H |
| 4.7~5.5 ppm | —Si—$\overline{CH_2}$—CH$_2$—CH$_2$—O—CON$\underline{H}$— 6H |
| 5.6~6.5 ppm | —C$\underline{H}$=$\overline{CH_2}$ 18H |

Example 2

The procedures of Example 1 were repeated except that 11.9 grams of the compound represented by the following formula (20) instead of 2-allyloxyethanol and 7.05 grams of acryloyloxyethyl isocyanate were added to 50.0 grams of compound I under a dry air atmosphere in a 100 ml three-necked flask equipped with a reflux device and a stirrer.

Obtained were 56.1 grams of the compound represented by the following formula (21).

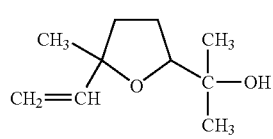

(20)

-continued (21)

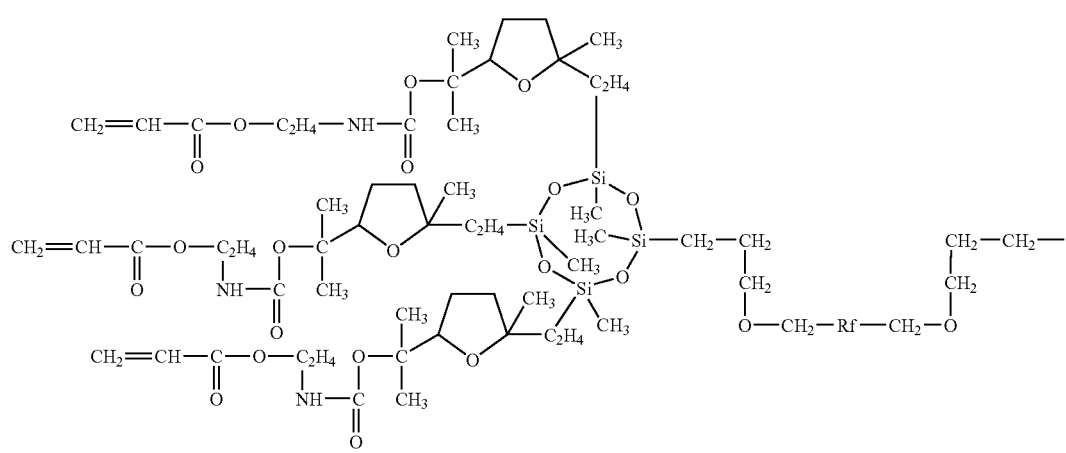

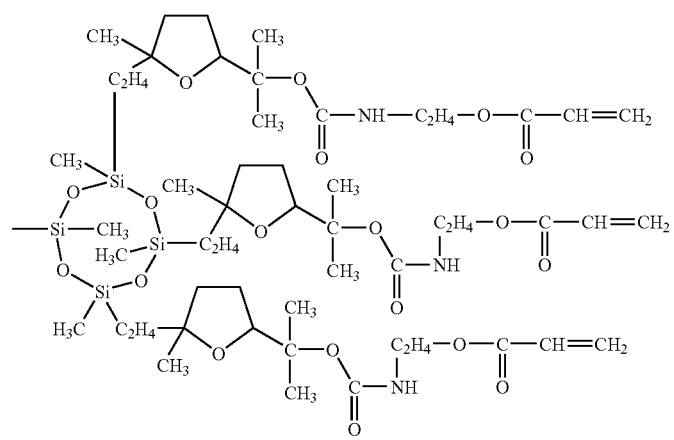

Chemical shifts in ¹H-NMR spectrum are shown in Table 2. (Measuring device: JMN-LA300W ex JEOL, solvent: CDCl₃)

TABLE 2

| Shift (TMS Reference) | |
|---|---|
| 0~0.2 ppm | —Si—C$\underline{H_3}$ 24H |
| 0.4~0.7 pmm | —Si—C$\underline{H_2}$—CH₂— 16H |
| 1.1~1.3 pmm | ≡C—C$\underline{H_3}$ 18H |
| 1.4~1.9 pmm | —C—(C$\underline{H_3}$)—₂ 36H |
|  | —Si—C$\underline{H_2}$—CH₂— 16H |
|  | —Si—CH₂—C$\underline{H_2}$—C(CH₃)= 12H |
|  | 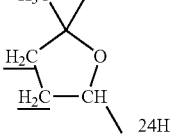 24H |

TABLE 2-continued

| Shift (TMS Reference) | |
|---|---|
| 3.4~3.9 pmm | —Si—C$\underline{H_2}$—C$\underline{H_2}$—C$\underline{H_2}$—O— 4H |
|  | —(CH₃)₂—O—CONH—C$\underline{H_2}$—CH₂—CO— 12H |
|  | 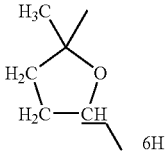 6H |
|  | —O—C$\underline{H_2}$—CF₂— 4H |
| 4.0~4.2 pm | —(C$\underline{H_3}$)—₂—O—CONH—CH₂—C$\underline{H_2}$—O—CO— 12H |
| 4.8~5.2 ppm | —Si—CH₂—CH₂—CH₂—O—CON$\underline{H}$— 6H |
| 5.8~6.56 ppm | —C$\underline{H}$=C$\underline{H_2}$ 18H |

Comparative Example

To a 100 ml three-necked flask equipped with a reflux device and a stirrer were fed 50.0 grams of fluorine-containing cyclic siloxane represented by the following formula (22),

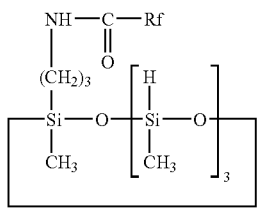
(22)

wherein $R^f$ is the following group

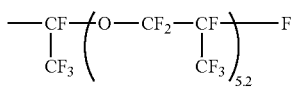

and 20.0 grams of toluene under a dry air atmosphere and heated to 90 degrees C. with stirring. Then, 9.75 grams of the polyoxyethylene methyl allyl ether represented by the following formula (23), $$CH_2=CH-CH_2O-(CH_2CH_2O)_{4.5}CH_3 \quad (23)$$

and 0.0110 gram of a solution of chloroplatinic acid/vinyl siloxane complex in toluene (Pt content: $2.73 \times 10^{-8}$ mole) were added dropwise over 1 hour and stirred at 90 degrees C. for 12 hours.

Separately, to a 100 ml three-necked flask equipped with a reflux device and a stirrer were added 16.9 grams of allyl alcohol and heated to 90 degrees C., to which, then, the afore-mentioned reaction solution which had been cooled to room temperature was added dropwise over three hours and stirred at 90 degrees C. for 16 hours. The reaction solution obtained was treated under a pressure of 6 Torr at 100 degrees C. for 2 hours to remove the unreacted allyl alcohol.

To 60.0 grams of the compound obtained were added 7.01 grams of 2-isocyanatoethylacrylate and 0.010 gram of dioctyltin laurate under a dry air atmosphere, and stirred at 25 degrees C. for 12 hours to obtain a compound having the average composition represented by the following formula (24), hereinafter referred to as "compound IV".

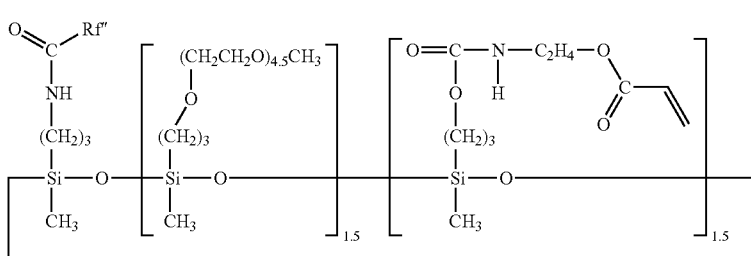
(24)

Evaluation on the Compositions for a Hard Coat

The compounds obtained in the Examples and the Comparative Example were blended in the following formulation shown in Table 3 to prepare solutions. As a blank, a solution which did not contain any additive was also prepared.

TABLE 3

| | |
|---|---|
| Tetra-functional acrylate (EBECRY 40, ex Daicel-Cytec Company Ltd.) | 100 parts by mass |
| 1-Hydroxycyclohexylphenylketone (Irgacure 184, ex Chiba Japan) | 3 parts by mass |
| Additive (Compound of Example 1 or 2, or Comparative Example) | 3 parts by mass |

Each solution which contained the additive of Examples 1 or 2, or the Comparative Example was applied by spin coating on a glass plate. This was irradiated with ultraviolet rays of 1.6 J/cm² by an ultraviolet irradiation device of a conveyer type, ex Panasonic Electric Works Co., Ldt., to form a cured film. Each film was visually observed to evaluate its appearance. A contact angle with water, a contact angle with oleic acid and a falling angle of oleic acid were measured on a contact angle meter, ex Kyowa Interface Science Co., Ltd.

Repellency to ink of a felt pen was evaluated by drawing a line on the surface with an oil-based felt pen, High Macky, ex Zebra Co., Ltd., and visually observing how much the ink was repelled. A coefficient of dynamic friction to Bemcot, ex Asahi Kasei, was measured by a surface tester, ex SHINTO Scientific Co., Ltd.

Table 4 shows the results of the evaluation of the surfaces which were treated with each hard coat.

TABLE 4

| | Additive | | | |
|---|---|---|---|---|
| | Compound of Example 1 | Compound of Example 2 | Compound of the Comparative Example | None |
| Appearance | Transparent and colorless | Transparent and colorless | Transparent and colorless | Transparent and colorless |
| Contact angle with water in degrees | 107 | 109 | 106 | 63 |
| Contact angle with oleic acid in degrees | 72 | 72 | 72 | 24 |
| Falling angle of oleic acid in degrees | 3 | 3 | 11 | Impossible to measure |

TABLE 4-continued

| | Additive | | | |
|---|---|---|---|---|
| | Compound of Example 1 | Compound of Example 2 | Compound of the Comparative Example | None |
| Coefficient of dynamic friction | 0.05 | 0.06 | 0.40 | 0.37 |
| Felt pen ink repellency | Very good | Very good | Good | Not repelled |

Industrial Applicability

As shown in Table 4, the present compound shows a lower coefficient of dynamic friction than that of the compound of the Comparative Example and can give good properties in a falling angle of oleic acid, felt pen ink repellency and a sliding property and, therefore, can be used as an additive in compositions for surface hard coats for, for instance, glass, resins, films, paper, metals, ceramics and wood; in compositions for surface-protecting films for printed materials; and in paint compositions.

The invention claimed is:

1. A perfluoropolyether group-containing acrylate compound represented by the following formula (1):

$$X^1-[Z-Rf-Z-X^2]_v-Z-Rf-Z-X^1 \quad (1)$$

wherein Rf is a divalent perfluoropolyether group with a molecular weight of from 500 to 30000, optionally having branched structure;

$X^1$ is, independently of each other, a group represented by the following formula (2):

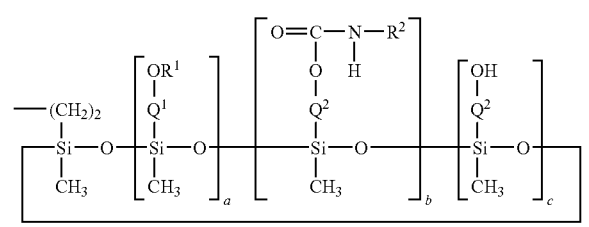

(2)

wherein a and c are an integer of from 0 to 4;
b is an integer of from 1 to 4, provided that a total of a, b and c is 2, 3 or 4;
$R^1$ is, independently of each other, a group represented by the following formula (3),

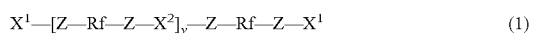

(3)

wherein d, e, f and g are, independently of each other, an integer of from 0 to 20, provided that a molecular weight of $R^1$ is in a range of 30 to 600;
the repeating units may be sequenced at random; and
$R^3$ is a saturated or unsaturated hydrocarbon residue having 1 to 10 carbon atoms;
$R^2$ is an acryl group- or alpha-substituted acryl group-containing group represented by the following formula (4):

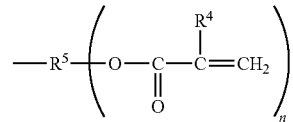

(4)

wherein $R^4$ is, independently of each other, a hydrogen atom, a fluorine atom, a methyl group or a trifluoromethyl group;
$R^5$ is a divalent or trivalent linking group having 1 to 18 carbon atoms, optionally having an ether bond and/or ester bond; and
n is an integer of 1 or 2;
$Q^1$ and $Q^2$ may be same with or different from each other and are a divalent linking group with 3 to 20 carbon atoms, optionally having an ether bond, an ester bond, an amide bond or a urethane bond and optionally having cyclic or branched structure;
$X^2$ is, independently of each other, a group represented by the following formula (5)

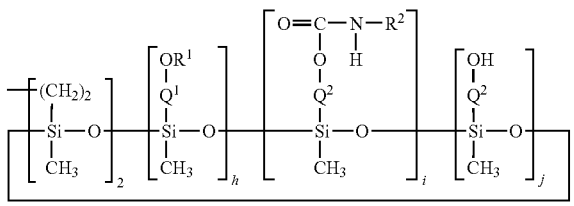

(5)

wherein $R^1$, $R^2$, $Q^1$ and $Q^2$ are as defined above;
h, i and j are an integer of from 0 to 3, provided that a total of h, i and j is an integer of from 1 to 3; and
the repeating units may be sequenced at random;
Z is a divalent organic group, optionally containing an oxygen atom, a nitrogen atom or a fluorine atom and unsaturated bond, and optionally having cyclic structure; and
v is an integer of from 0 to 5.

2. The acrylate compound according to claim 1, wherein Rf comprises 1 to 500 repeating units represented by the following formula:

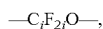

wherein i is, independently of each other among the units, an integer of from 1 to 6.

3. The acrylate compound according to claim 1, wherein Rf is selected from the group consisting of the groups represented by the following formulas (6) to (8):

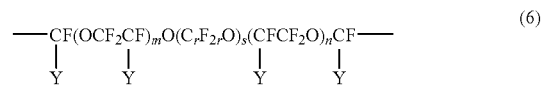

(6)

wherein Y is, independently of each other, a fluorine atom or a $CF_3$ group; r is an integer of from 2 to 6; m and n are each an integer of from 0 to 200, provided that a total of m and n is 2 to 200; s is an integer of from 0 to 6, wherein the repeating units may be sequenced at random;

(7)

wherein j is an integer of from 1 to 3 and k is an integer of from 1 to 200; and

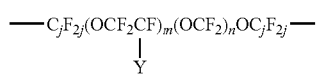 (8)

wherein Y is a fluorine atom or a $CF_3$ group; j is an integer of from 1 to 3; m and n are each integer of from 0 to 200, provided that a total of m and n is from 2 to 200; and the repeating units may be sequenced at random.

4. The acrylate compound according to claim 1, wherein Z is one of the following groups.

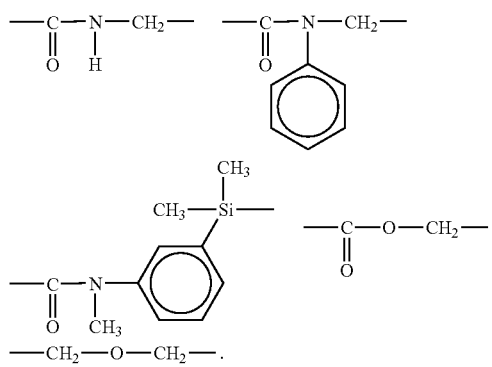

5. The acrylate compound according to claim 1, wherein $Q^1$ is any one of the following groups.

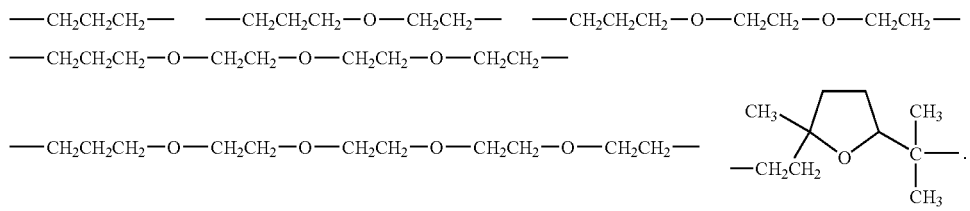

6. The acrylate compound according to claim 1, wherein $R^2$ is any one of the following groups.

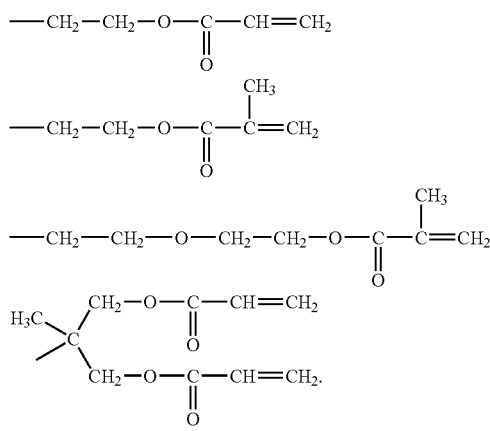

7. The acrylate compound according to claim 1, wherein $R^1$ is a group represented by the following formula:

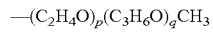

wherein p and q are an integer of from 0 to 20, provided that a total of p and q is from 1 to 40 and the propylene group may be branched, and the repeating units may be sequenced at random.

8. A composition for a hard coat, comprising the acrylate compound according to claim 1.

9. The composition for a hard coat according to claim 8, wherein a major component of the composition for a hard coat is urethane acrylate.

10. The acrylate compound according to claim 2, wherein Rf is selected from the group consisting of the groups represented by the following formulas (6) to (8):

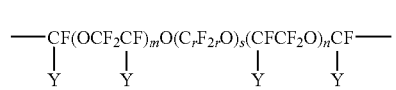 (6)

wherein Y is, independently of each other, a fluorine atom or a $CF_3$ group; r is an integer of from 2 to 6; m and n are each an integer of from 0 to 200, provided that a total of m and n is 2 to 200; s is an integer of from 0 to 6, wherein the repeating units may be sequenced at random;

 (7)

wherein j is an integer of from 1 to 3 and k is an integer of from 1 to 200; and

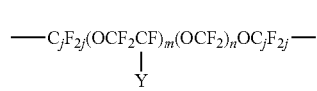 (8)

wherein Y is a fluorine atom or a $CF_3$ group; j is an integer of from 1 to 3; m and n are each integer of from 0 to 200, provided that a total of m and n is from 2 to 200; and the repeating units may be sequenced at random.

11. The acrylate compound according to claim 2, wherein Z is one of the following groups.

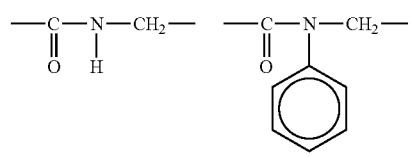

-continued

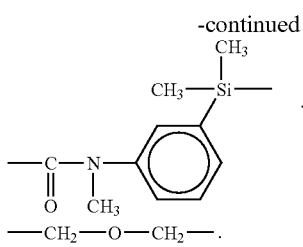

12. The acrylate compound according to claim 3, wherein Z is one of the following groups.

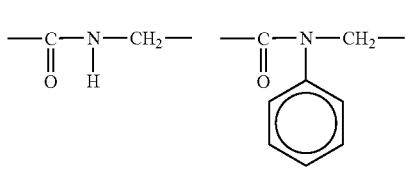

-continued

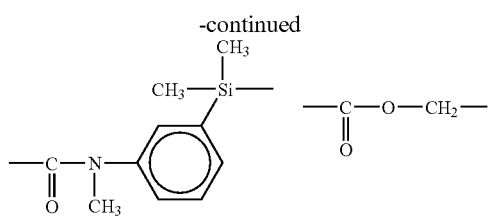

—CH₂—O—CH₂—.

13. The acrylate compound according to claim 2, wherein Q¹ is any one of the following groups.

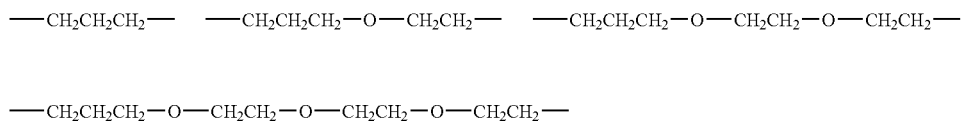

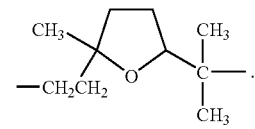

14. The acrylate compound according to claim 3, wherein Q¹ is any one of the following groups.

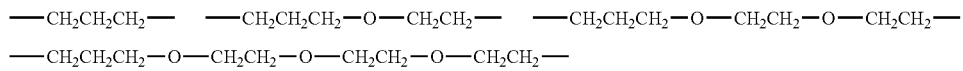

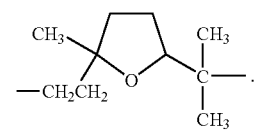

15. The acrylate compound according to claim 4, wherein Q¹ is any one of the following groups.

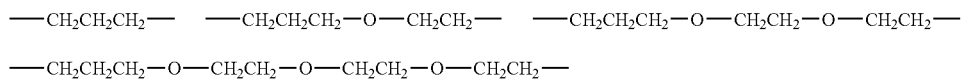

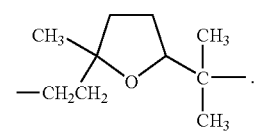

16. The acrylate compound according to claim 2, wherein $R^2$ is any one of the following groups.

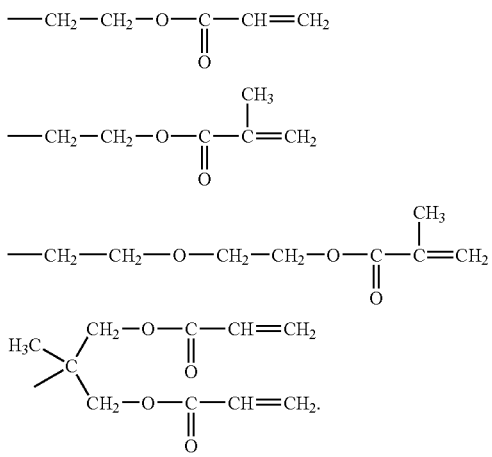

17. The acrylate compound according to claim 3, wherein $R^2$ is any one of the following groups.

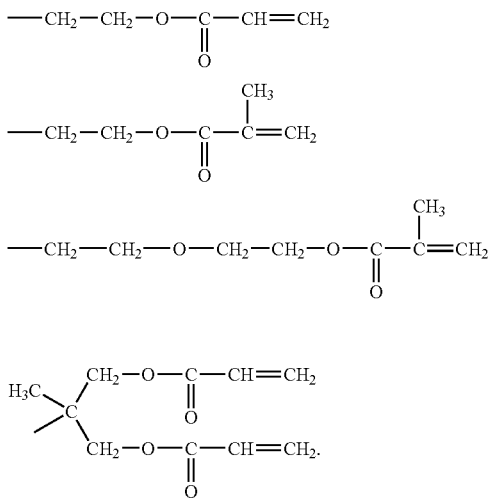

18. The acrylate compound according to claim 4, wherein $R^2$ is any one of the following groups.

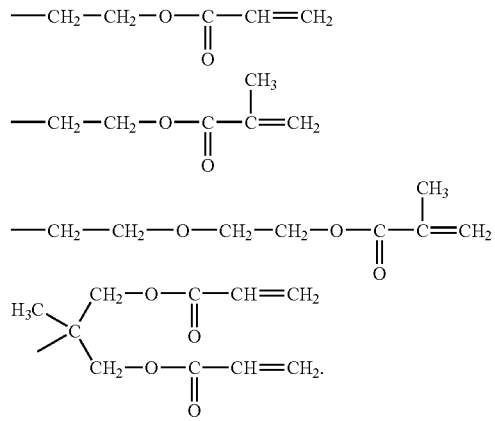

19. The acrylate compound according to claim 5, wherein $R^2$ is any one of the following groups.

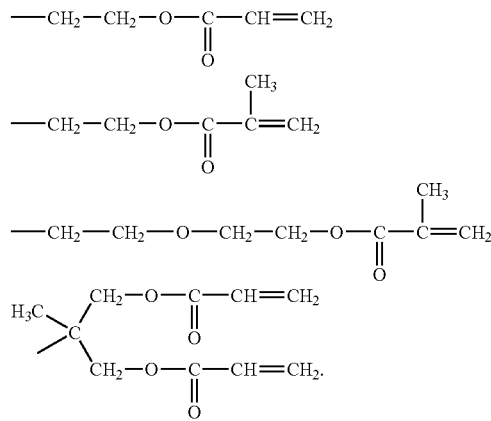

20. The acrylate compound according to claim 2, wherein $R^1$ is a group represented by the following formula:

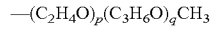

wherein p and q are an integer of from 0 to 20, provided that a total of p and q is from 1 to 40 and the propylene group may be branched, and the repeating units may be sequenced at random.

* * * * *